United States Patent [19]

McGuire

[11] Patent Number: 5,464,407
[45] Date of Patent: Nov. 7, 1995

[54] FLEXIBLE SURGICAL SCREWDRIVER AND METHODS OF ARTHROSCOPIC LIGAMENT RECONSTRUCTION

[76] Inventor: David A. McGuire, 3418 Lakeside Dr., Anchorage, Ak. 99515

[21] Appl. No.: 340,790

[22] Filed: Nov. 16, 1994

Related U.S. Application Data

[63] Continuation-in-part of Ser. No. 956,733, Oct. 2, 1992, Pat. No. 5,391,170, which is a continuation-in-part of Ser. No. 806,906, Dec. 13, 1991, Pat. No. 5,257,996, and a continuation-in-part of Ser. No. 839,466, Feb. 19, 1991.

[51] Int. Cl.$^6$ ........................................................ A61F 5/00
[52] U.S. Cl. ........................... 606/86; 606/104; 81/177.6
[58] Field of Search ............................. 606/86, 87, 88, 606/96, 97, 98, 72–78, 104; 81/177.6, 436

[56] References Cited

U.S. PATENT DOCUMENTS

| | | | |
|---|---|---|---|
| 877,571 | 1/1908 | Larson | 81/57.29 |
| 933,639 | 9/1909 | Frink . | |
| 1,199,823 | 10/1916 | Sadtler . | |
| 1,398,116 | 11/1921 | Root . | |
| 1,428,282 | 9/1922 | Glabaznya . | |
| 1,653,995 | 12/1927 | English | 81/177.6 |
| 1,903,660 | 4/1933 | Smith | 81/177.6 |
| 2,042,376 | 5/1936 | Balga | 279/89 |
| 2,267,925 | 12/1941 | Johnston | 128/92 |
| 2,570,465 | 10/1951 | Lundholm | 128/92 |
| 3,232,151 | 2/1966 | Blachowski | 81/177 |
| 3,351,054 | 11/1967 | Florek | 128/83 |
| 3,604,486 | 9/1971 | Henry | 42/50 |
| 3,696,694 | 10/1972 | Boro | 81/57.27 |
| 3,788,169 | 1/1974 | Nakayama | 81/177 UJ |
| 3,892,232 | 7/1975 | Neufeld | 128/92 |
| 4,140,111 | 2/1979 | Morrill | 128/92 E |
| 4,202,067 | 5/1980 | Stamatovic | 15/28 |
| 4,331,413 | 5/1982 | Hoen | 411/44 |
| 4,350,169 | 9/1982 | Dutcher et al. | 128/783 |
| 4,381,770 | 5/1983 | Neufeld | 128/92 BA |
| 4,383,527 | 5/1983 | Asnis et al. | 128/92 EB |
| 4,441,563 | 4/1984 | Walton, II | 173/163 |
| 4,450,835 | 5/1984 | Asnis et al. | 128/92 EB |
| 4,483,562 | 11/1984 | Schoolman | 294/19 |
| 4,515,943 | 5/1985 | Gray | 81/57.22 |
| 4,611,515 | 9/1986 | Marbourg, Jr. | 81/454 |
| 4,620,458 | 11/1986 | Schmidek | 81/57.28 |
| 4,643,052 | 2/1987 | Badiali | 81/57.28 |
| 4,706,659 | 11/1987 | Matthews et al. | 128/92 |
| 4,712,542 | 12/1987 | Daniel et al. | 623/13 |
| 4,738,255 | 4/1988 | Goble . | |
| 4,772,286 | 9/1988 | Goble et al. | 623/13 |
| 4,781,182 | 11/1988 | Purnell et al. | 128/92 VD |
| 4,911,041 | 3/1990 | Jones et al. | 81/487 |

(List continued on next page.)

FOREIGN PATENT DOCUMENTS

| | | |
|---|---|---|
| 645252 | 7/1992 | Canada . |
| 1430026 | 3/1976 | Germany . |
| 0246326 | 9/1947 | Sweden ............ 81/177.6 |
| 2250441B | 6/1992 | United Kingdom . |

OTHER PUBLICATIONS

Burnett and Fowler; *Reconstruction of the Anterior Cruciate Ligament: Historical Overview*, Jan. 1985, Orthopedic Clinics of North America, vol. 16, No. 1, pp. 143–157.

*Technique for Endoscopic Patellar Tendon Bone Block Fixation Using a Cannulated Interference Screw System.*

Statak; *Soft Tissue Attachment Device*, by Zimmer, Inc. 1988.

*Primary Examiner*—Michael A. Brown
*Attorney, Agent, or Firm*—Bromberg & Sunstein

[57] ABSTRACT

A surgical screwdriver for inserting bone screws in bone tunnels in ligament reconstruction has, in a preferred embodiment, a flexible cannulated operating shaft. The shaft is formed by concentric coils including at least one clockwise helical coil and at least one counterclockwise helical coil. The screwdriver is used in methods of arthroscopic cruciate ligament reconstruction including the steps of introducing the screwdriver along a guide wire through a portal that is offset from the longitudinal axis of a bone tunnel and driving an interference screw mounted on the driver in the bone tunnel to fixate a bone block in the bone tunnel.

11 Claims, 8 Drawing Sheets

U.S. PATENT DOCUMENTS

| | | | |
|---|---|---|---|
| 4,927,421 | 5/1990 | Goble et al. | 606/73 |
| 4,947,942 | 8/1990 | Lightle et al. | 173/163 |
| 4,950,270 | 8/1990 | Bowman et al. | 606/72 |
| 5,041,119 | 8/1991 | Frigg et al. | 606/96 |
| 5,069,569 | 12/1991 | Lieser | 403/57 |
| 5,139,520 | 8/1992 | Rosenberg | 623/13 |
| 5,391,170 | 2/1995 | McGuire et al. | 606/86 |
| 5,391,171 | 2/1995 | Schmieding | 606/104 |

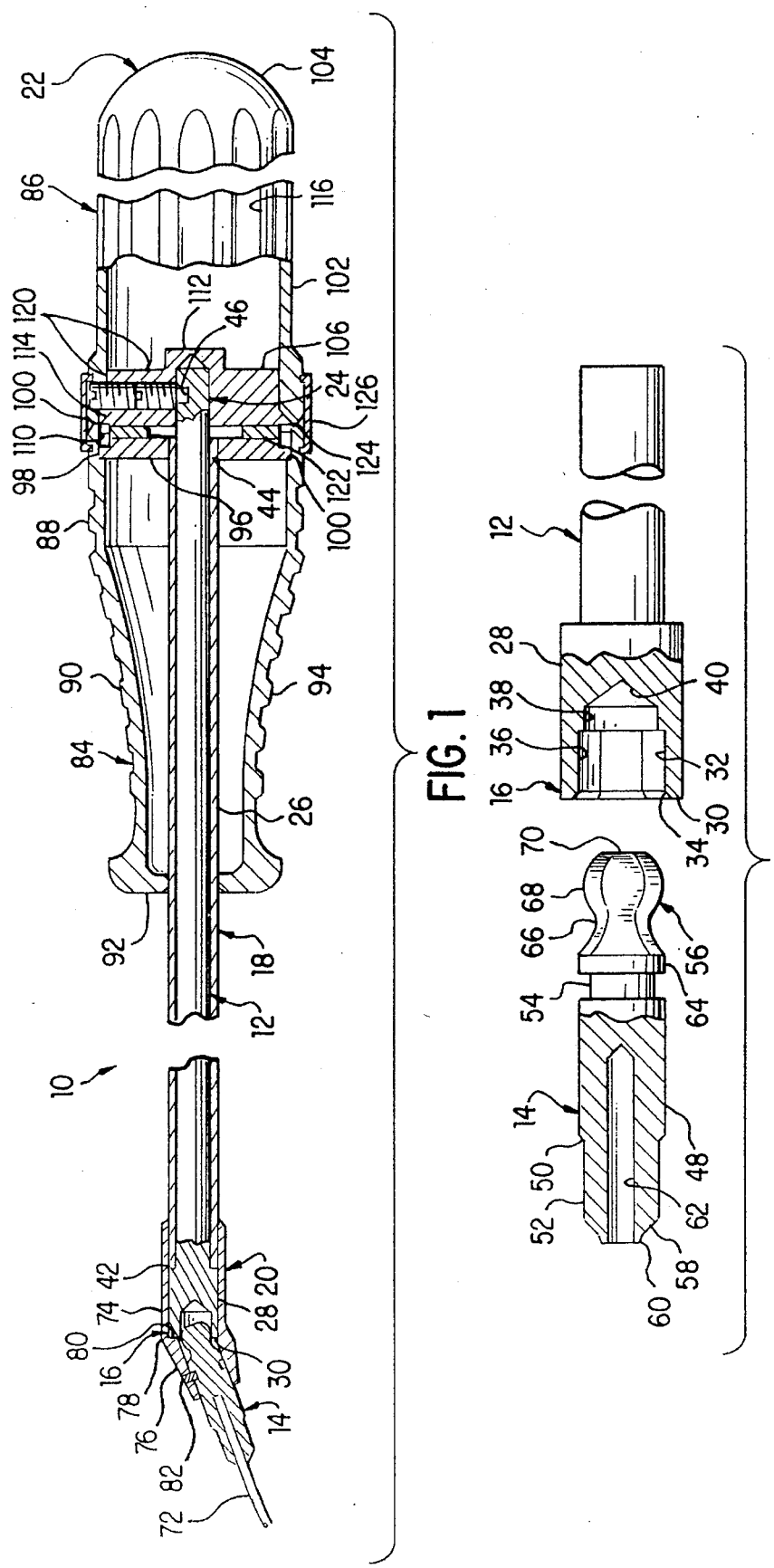

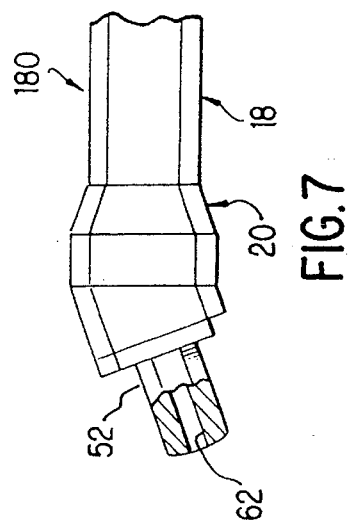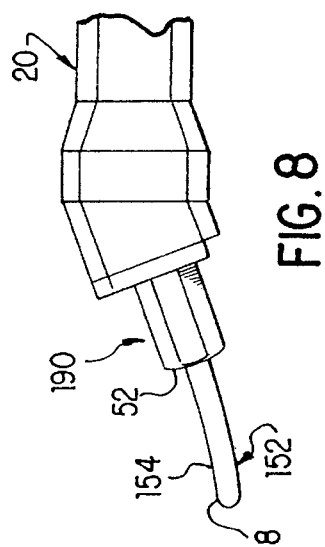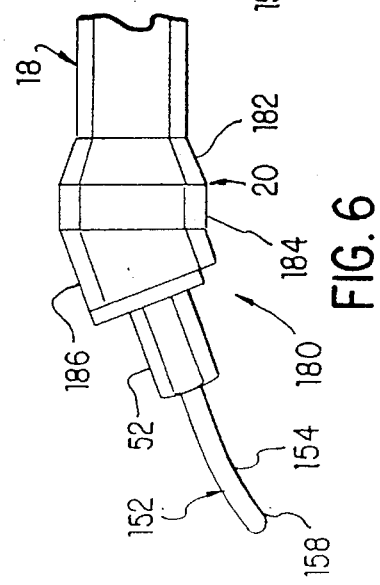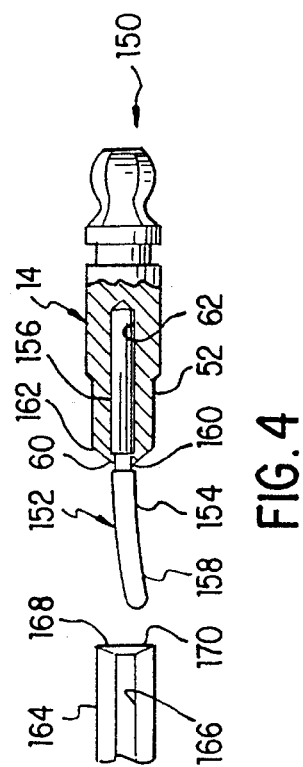

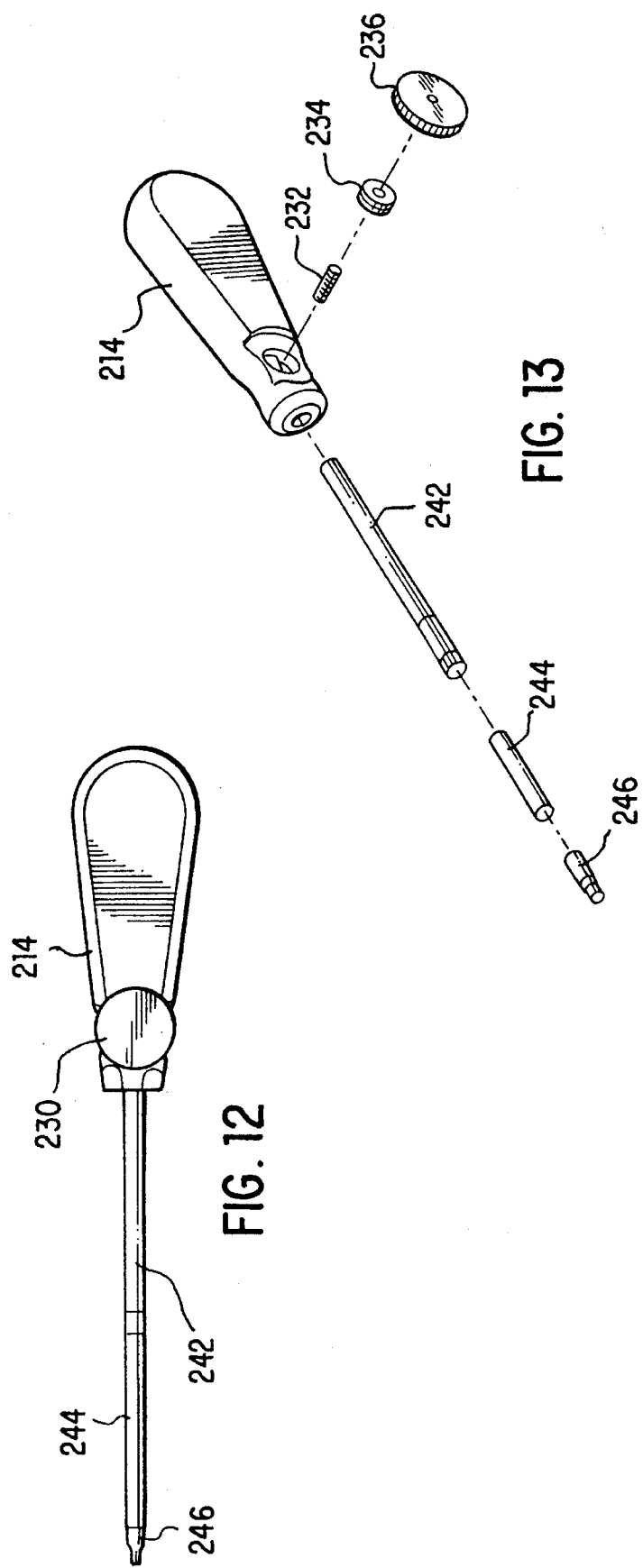

FLEXIBLE SURGICAL SCREWDRIVER AND METHODS OF ARTHROSCOPIC LIGAMENT RECONSTRUCTION

This application is a continuation-in-part of application No. 07/956,733 filed Oct. 2, 1992 entitled "Angled Surgical Screw Driver and Methods of Arthroscope Ligament Reconstruction", now U.S. Pat. No. 5,391,170, which in turn is a continuation-in-part of application Ser. No. 07/806,906, filed Dec. 13, 1991, for an invention entitled "Surgical Pin Passer", now U.S. Pat. No. 5,257,996 and Ser. No. 07/839,466, filed Feb. 19, 1992, for an invention entitled "Femoral Guide and Methods of Precisely Forming Bone Tunnels in Cruciate Ligament Reconstruction of the Knee." These related applications are hereby incorporated herein by reference.

TECHNICAL FIELD

The present invention pertains to surgical screwdrivers for inserting bone screws and, more particularly, to surgical screwdrivers for inserting interference bone fixation screws in bone tunnels and to methods of performing arthroscopic cruciate ligament reconstruction of the knee.

BACKGROUND ART

Various surgical procedures utilize devices to fixate anatomical tissue for healing. An example of a fixation device is an interference bone fixation screw, commonly referred to throughout the present description as "interference screw", used to fixate ligaments within bone tunnels during cruciate ligament reconstruction of the knee.

A surgical screwdriver is commonly used to insert bone screws. This form of screwdriver has a rotatable drive shaft for rotating the screw, and advancing it along the longitudinal axis of the driver. The driver cooperatively engages with a drive recess, within the interference screw, to help achieve axial alignment of the screw with the drive shaft of the screwdriver.

In cruciate ligament reconstruction, the interference screw is inserted into tandem isometrically positioned bone tunnels formed in the tibia and femur. A prosthetic ligament graft affixed to bone blocks at each end is inserted into the bone tunnel such that the ligament extends across the knee joint in the anatomical position of the cruciate ligament. The bone blocks are fixated within the bone tunnel by interference screws. Each interference screw is inserted in the bone tunnel so as to be disposed laterally between the walls of the bone tunnel and the bone block. Successful cruciate ligament reconstruction depends on the proper insertion of the interference screw along the longitudinal axis of the bone tunnel, parallel to both the tunnel walls and the bone block. Incorrect insertion of the interference screw causes screw divergence, resulting in increased difficulty in advancing the screw in the bone tunnel and reduced contact between the threads on the screw and the bone block. In addition, screw convergence can result in crushing or fracturing of the ligament and dislocation of the bone block, causing deviation of the ligament from an accurate, pre-established isometric position.

Cruciate ligament reconstruction is commonly performed as an open surgical procedure. Incisions on the order of 10 inches in length are utilized to access the knee joint. These relatively long incisions are required to provide room for the surgical screwdriver to approach the tibial and femoral bone tunnels from directions aligned with the longitudinal axes of the bone tunnels and thereby to permit the driver to drive the interference screws effectively in a direction parallel with the bone block and the walls of the bone tunnels.

Open surgery possesses numerous disadvantageous compared to closed surgery or less invasive (arthroscopic) surgery for ligament reconstruction. These disadvantages include possible violation of mechanoreceptors in the knee, desiccation of articular cartilage of the joint, increased tissue trauma resulting from incisions accompanied by increased patient discomfort and delayed post surgical mobility. In addition, hospitalization and rehabilitation times may be prolonged.

Accordingly, it is desirable to develop methods for performing cruciate ligament reconstruction that are less invasive, such as arthroscopic surgical procedures. Narrow portals are made with a puncture or stab wound in tissue adjacent to the knee of sufficient size to permit insertion of surgical instruments at the knee joint with the knee being visualized with an arthroscope. An arthroscope is here defined as any instrument for insertion into the cavity of a joint in order to inspect its contents. An example of an arthroscope is a fiberscope, which uses fiber optics to transmit images from the interior of the joint.

A method of arthroscopic cruciate ligament reconstruction can provide many benefits over open surgery, including reduced tissue trauma, decreased patient discomfort, earlier and aggressive range of motion and weight bearing without loss of fixation, reduced rehabilitation time and elimination of hospitalization because the procedures can be performed on an out-patient basis.

The limitations on maneuverability imposed by arthroscopic cruciate ligament reconstruction and the location of the arthroscopic portals in tissue adjacent to the knee mean that conventional drivers with straight drive shafts, which are used for placing interference screws into bone tunnels through incisions during open surgery, are not suited for this procedure.

Indeed, the anteromedial and anterolateral portals are angularly offset from the longitudinal axis of the femoral bone tunnel and therefore the direction of approach from such portals to the femoral bone tunnel to insert an interference screw is angularly offset also. The femoral bone tunnel opens on the femoral condyle at a site near the attachment site of the cruciate ligament. Longitudinal alignment of the screwdriver with the opening of the femoral bone tunnel on the femoral condyle is difficult using conventional surgical drivers when the approach is made through the arthroscopic portals. This in turn presents difficulties in driving the screw parallel with the longitudinal axis of the femoral bone tunnel and the bone block in the tunnel.

Attempting to force the driver into parallelism with the longitudinal axis of the femoral bone tunnel runs a number of serious risks, including the possible breakage of the shaft of the driver at the knee; disengagement of the interference screws from the driver during manipulation and their contact with adjacent knee structures, followed by loss of the interference screw in the knee; and misalignment of the interference screw between the wall of the femoral bone tunnel and the bone block.

One compromise approach to the problem of location of arthroscopic portals is to introduce additional portals specifically for the purpose of inserting interference screws into the bone tunnel. One approach is to insert the interference screw through openings of the femoral bone tunnels on the lateral femoral cortex via portals placed proximally and laterally on the patients' thigh. This approach precludes the use of blind or closed end femoral bone tunnels. Alternatively, interference screws can be inserted through openings in the femoral condyle after their introduction through the tibial bone tunnels.

Angled drivers have been used in industrial applications as wrenches and screwdrivers, and exemplary of such devices are U.S. Pat. Nos. 4,643,052 to Badiali, 4,620,458 to Schmidek, 3,788,169 to Nakayama, 3,696,694 to Boro, 3,604,486 to Henry, 3,232,151 to Blachowski, 2,042,376 to Balga, 1,428,282 to Glabaznya, 1,398,116 to Root, 1,199,823 to Sadtler, 933,639 to Frink and 877,571 to Larson. In medical applications, angled drivers have been used in power tools such as drills, and U.S. Pat. Nos. 5,041,119 to Frigg et al and 4,947,942 to Lightle et al are illustrative of angled, surgical power drills.

Prior art angled surgical drivers are unsuitable for use in least invasive, or endoscopic, surgical procedures to insert interference screws in bone tunnels directly from portals not aligned parallel with longitudinal axes of the bone tunnels. Moreover, angled surgical drivers in the prior art cannot effectively hold screws captive for insertion into the body through endoscopic size portals.

SUMMARY OF THE INVENTION

The present invention provides, in one embodiment, a flexible surgical screwdriver for driving an interference screw into bone so that the screw is securely supported by the driver until insertion has been completed. The flexible surgical driver permits access from an arthroscopic portal not aligned parallel with a longitudinal axis of the bone tunnel to place the interference screw parallel with the walls of the bone tunnel and the bone block while driving the screw from a direction angularly disposed with the tunnel wall.

One embodiment has a flexible shaft, a handle mounted to the flexible shaft for applying rotational force to the shaft, and a drive head mounted on the flexible shaft. The flexible shaft and handle are cannulated according to an embodiment for use with cannulated interference screws. The cannulated screw and driver are guided over a guide wire into position along the bone tunnel wall.

The flexible shaft may be formed by concentric coil springs, coiled in opposite directions. This permits the application of torque through the drive shaft in a clockwise or counterclockwise direction. Whereas one spring will transmit torque in one of the directions, an oppositely coiled spring will transmit torque in the opposite direction.

An alternative embodiment of a screwdriver in accordance with the present invention permitting access from an arthroscopic portal not aligned parallel with a bone tunnel is an angled driver. The drive shaft is mounted on the operating shaft at an angle of approximately 20° with respect to the longitudinal axis of the operating shaft. An indicator on the handle allows orientation of the drive tip to be identified externally of the body, when the drive tip is inserted in the body through portals of minimal size. The angled driver may be used without being cannulated. In this case, a retaining mechanism for holding a cannulated interference screw captive on the drive shaft prior to screw insertion includes a wire having a proximal cylindrical section secured in a passage in the drive tip aligned with the longitudinal axis of the drive shaft and a distal cylindrical section that protrudes beyond the drive tip to be received in the cannula of the interference screw. The distal cylindrical section of the retaining mechanism is formed with a thermally set, slight curve or kink to hold the screw temporarily in place on the drive tip.

The procedure in accordance with a preferred embodiment of the present invention advantageously eliminates the step of penetrating the lateral femoral cortex and permits a countersink of the screw below the opening of the femoral bone tunnel on the femoral condyle. The procedure can be performed with fewer and smaller portals. In fact, the anteromedial and anterolateral portals formed for procedures preparatory to graft fixation can be utilized to directly insert bone screws in femoral bone tunnels. In addition, hyperflexion of the knee in arthroscopic anterior cruciate ligament reconstruction can be eliminated.

The surgical instrument provided in a preferred embodiment of the invention is designed to avoid drive shaft breakage, loss of interference screws at the knee joint, and to enhance screw insertion and driver positioning. In addition, screw divergence is minimized and maximum thread purchase along the length of the bone block is ensured. The embodiment is of unified construction for easy cleaning and sterilization with right and left knee compatibility. The embodiment employs a lightweight, ergonomic handle providing a balanced feel for the surgeon.

BRIEF DESCRIPTION OF THE DRAWINGS

These and other features of the present invention may be more readily understood by reference to the following description, taken in conjunction with the accompanying drawings, in which:

FIG. 1 is a broken side view, partly in longitudinal section, of an embodiment of an angled surgical screwdriver according to the present invention, showing an interference screw mounted on the screwdriver;

FIG. 2 is an exploded, broken side view, partly in section, of the distal end of the angled surgical screwdriver of FIG. 1;

FIG. 4 is a broken side view, partly in section, of the drive shaft of a related embodiment of an angled surgical screwdriver according to the present invention, showing a retaining mechanism on the drive shaft and an end of a forming tool for mounting the retaining mechanism on the drive shaft;

FIG. 6 is a broken side view of the distal end of a further embodiment of an angled surgical screwdriver according to the present invention;

FIG. 7 is a broken side view, partly in section, of the drive shaft for the angled surgical screwdriver of FIG. 6;

FIG. 8 is a broken side view of the distal end of another embodiment of an angled surgical screwdriver according to the present invention;

FIG. 12 is a plan view of a further embodiment of a cannulated flexible screwdriver of the present invention;

FIG. 13 is an exploded view of the screwdriver of FIG. 12; and

DESCRIPTION OF SPECIFIC EMBODIMENTS

Figure 5:
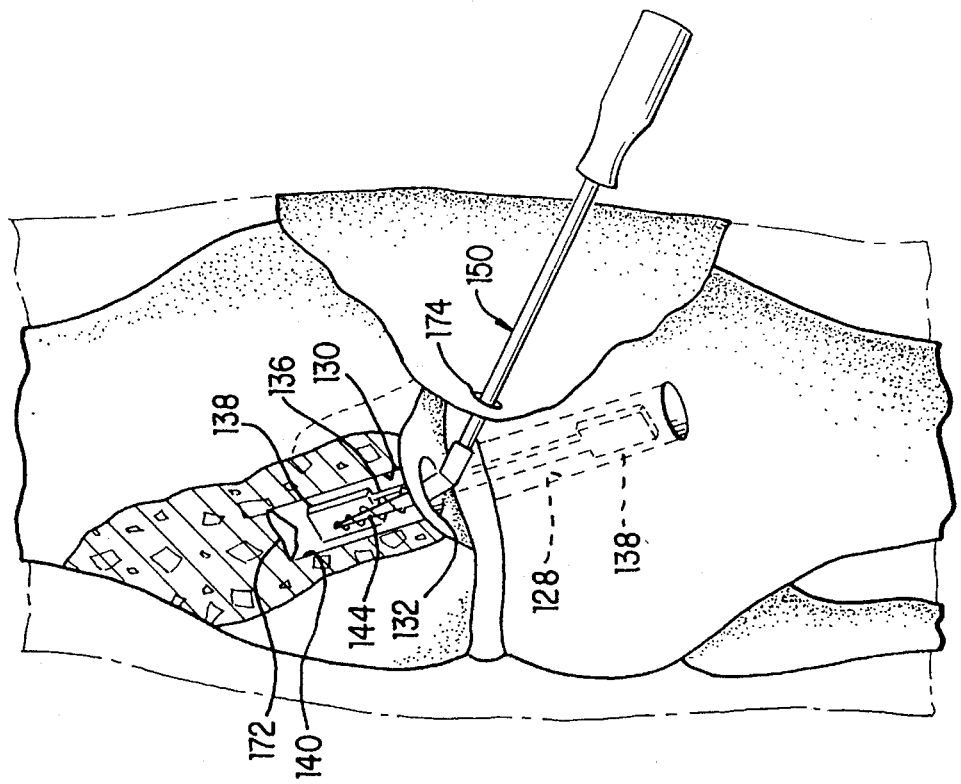
FIG. 5 is a front view, partly in section, of the knee, joint of a right knee positioned at substantially 90°, showing the angled surgical screwdriver of FIG. 4 inserting a bone screw in a closed end femoral bone tunnel via an anteromedial portal.

An angled surgical screwdriver 10 according to an embodiment of the present invention is illustrated in FIG. 1, and includes an elongate operating shaft 12 with a distal end 16 coupled to a drive shaft 14 and a proximal end 24 on which is mounted a movable portion of handle 22. Concentrically disposed around the operating shaft 12 is a sleeve 18, having a distal end 42, on which is mounted a drive head housing 20 and a proximal end 44 secured in a fixed portion of handle 22. Turning the movable portion of handle 22 with respect to the fixed portion thereof causes rotation of the drive shaft 14, which is disposed at an angle of approximately 20° from the axis of rotation of handle 22. The operation of the screwdriver 12 is described in further detail below.

The operating shaft 12 is preferably made of stainless steel with a cylindrical body terminating, at the distal end 16, at a distal end wall 30. Fitted concentrically around the distal end 16 is a cylindrical barrel 28, detail of which is shown in FIG. 2. A socket 32 is formed distally in barrel 28 in axial alignment with a longitudinal axis of the operating shaft 12 and, therefore, the longitudinal axis of the driver 10, as shown in FIGS. 1 and 2.

Socket 32 includes successively a tapered distal recess 34 at end wall 30, an intermediate recess 36, having a hexagonal configuration in cross-section, a cylindrical recess 38, and a conical proximal recess 40. The recesses are contiguous. Intermediate recess 36 is formed of six flat sides extending longitudinally in the barrel 28 from distal recess 34 to cylindrical recess 38. The cylindrical recess 38 has a diameter smaller than the diametric, cross-sectional dimension of the intermediate recess 36.

A ball mechanism 56 includes a cylindrical flange 64 joined to cylindrical neck 54, a curved neck 66 extending proximally from flange 64, and a ball 68 mounted on curved neck 66. The cylindrical flange 64 has an outer diameter that is substantially the same as the outer diameter of the cylindrical body 48 and larger than the diameter of the cylindrical neck 54, such that an annular recess is defined concentrically around the cylindrical neck 54 laterally between the body 48 and the flange 64 of the drive shaft 14. The ball 68 has a hexagonal configuration in cross-section, being formed of six curved surfaces extending proximally from curved neck 66 to an end surface 70. Ball 68 is configured to be received in socket 32 of the operating shaft 12 with the longitudinal axis of the drive shaft 14 disposed at an acute angle of approximately 20° with respect to the longitudinal axis of the operating shaft 12. Engagement of the ball 68 in the socket 32 causes rotation of the drive shaft 14 in response to rotation of the operating shaft 12.

Drive shaft 14 is preferably made of stainless steel and, as shown in FIGS. 1 and 2, includes a cylindrical body 48, a drive tip 52, and the ball mechanism 56, in axial alignment. The cylindrical body 48 is joined to the drive tip 52 at the distal end of a shoulder 50 tapered in a distal direction, the proximal end of shoulder 50 joining a neck 54, which in turn proximally joins the cylindrical body 48 to the ball mechanism 56. The drive tip 52 has a distally tapered shoulder 58 terminating distally at an annular, peripheral lip 60, and a cylindrical passage 62 is formed in the drive tip 52 to extend proximally, longitudinally from lip 60 in axial alignment with the longitudinal axis of the drive shaft.

One purpose of the drive tip 52 is to frictionally secure the end of a length of guide wire 72, such as a nitinol wire, as will be explained below, as shown in FIG. 1. Another purpose of the drive tip is to frictionally engage a screw. The drive tip 52 has an external configuration to frictionally engage a drive recess 143 of an interference bone fixation screw 144. The drive tip 52 can have various cross-sectional configurations—for example, multi-lobed or pronged, or hexagonal—corresponding to the configuration of the drive recess 143 of the fixation screw 144, so the screw will be rotated in bone with rotation of the drive shaft 14.

The cylindrical body 48 may be formed with the same cross-sectional configuration as, but slightly greater dimensions than, the drive tip 52, so as to frictionally engage the drive recess 143 of the screw 144, when, as shown in FIG. 1, the drive tip 52 is inserted deeply enough into the screw 144 to cause the body 48 portion to enter the drive recess 143.

In a preferred embodiment, the drive shaft 14 is prevented from being inserted into the drive recess 143 so far that the drive head housing 20 contacts the proximal end of screw 144. In this embodiment, the back end of the screw 144 is spaced distally from the drive head housing 20 to allow a portion (approximately 5 mm in one preferred embodiment) of the drive shaft 14 beyond the drive head housing 20 to be exposed. The exposed portion permits the screw 144 to be countersunk into a bone tunnel by an approximate additional amount equal to the length of the exposed portion.

The back end of the screw can be made to terminate distally of the drive head housing 20 in various ways. These include (a) making the distance from the lip 60 to the drive head housing 20 less than the length of the drive recess 143; or (b) forming the drive shaft 14 with external configurations or diametric dimensions limiting the distance that the drive shaft 14 can be inserted in the drive recess 143; or (c) providing a retaining mechanism on the drive shaft 14 that limits the distance that the drive shaft 14 can be inserted in the drive recess 143 as will be explained further below.

Drive head housing 20 is preferably made of stainless steel and includes a cylindrical section 74 and a distally tapered nose section 76 joined to the cylindrical section 74 at a bend 78, the nose section 76 extending angularly, distally from the cylindrical section 74. The wall of the cylindrical section 74 has a thickness that is substantially constant along the length of the cylindrical section with an inner diameter sized to closely receive the outer diameters of the cylindrical barrel 28 and the sleeve 18. The wall of the nose section 76 has a thickness that is greater than the wall thickness of the cylindrical section 74 at bend 78 to define an internal shoulder 80 serving as a stop for cylindrical barrel 28 when operating shaft 12 is disposed within the cylindrical section 74. The wall thickness of the nose section 76 tapers in a distal direction such that an internal, cylindrical passage of substantially constant cross-section is defined along the length of the nose section. The cylindrical passage of the nose section 76 is disposed at an angle with respect to the longitudinal axis of the cylindrical passage of the cylindrical section 74 that the angle of the drive shaft 14 with respect to the operating shaft 12.

A C-shaped clip 82 is mounted (by welding, for example, or simply by appropriate dimensions) in an annular slot in the nose section 76 and is received in the annular recess around neck 54 to prevent axial movement of the drive shaft 14 while allowing the drive shaft to rotate within the housing 20.

In a related embodiment of the angled surgical screwdriver shown in FIGS. 4, 6 and 8, the angled driver 150 is substantially the same as the angled driver 10 of FIG. 1, except that a retaining mechanism 152, for holding an interference bone fixation screw captive on the driver prior to insertion of the screw, is mounted on drive shaft 14. Retaining mechanism 152 includes a length of wire 154 (identified in FIGS. 6 and 8), such as a nitinol wire, having a proximal cylindrical section 156, which is joined to neck 160 at a shoulder 162, and a distal cylindrical section 158 joined to the proximal cylindrical section 156 by neck 160.

The neck 160 has an outer diameter that is smaller than the outer diameters of the proximal and distal cylindrical sections, which in turn are slightly smaller than the diameter of the cannula 145 in the interference bone fixation screw 144. The outer diameter of the proximal cylindrical section 156 is sufficient to be received in the passage 62 in the drive tip 52 of drive head 14. The distal cylindrical section 158 is formed with a thermally set, slight radius curve along its length. The length of the wire 154 that protrudes beyond the drive tip 52 when the proximal cylindrical section 156 is received therein is selected to allow the curved distal cylindrical section 158 to be disposed in the cannula 145 of the screw 144 and to provide frictional engagement with the walls forming the cannula 145 when the screw is placed upon the drive shaft 14, such as shown in FIG. 8.

The wire 154 is mounted on the drive shaft 14 by press fitting the proximal cylindrical section 156 in the passage 62 of the drive tip 52 in a manner such that the neck 160 is aligned with edge 60 of drive tip 52. In some instances, depending on the material from which tip 152 is made, a press fit is sufficient and there is no need for neck 160 or shoulder 162. In other instances, when a neck and shoulder structure is used, a forming tool 164 is useful.

Forming tool 164 has a longitudinal cavity 166 terminating at a recess 168 tapered in the distal direction. In use, the forming tool 164 is moved along the wire 154 in the direction of the drive shaft 14 until the end wall 170 abuts the drive tip 52. In that position, the forming tool is urged against the tip 52, and the forming tool's tapered recess 168 forces the lip 60 to grip neck 160, and this grip, along with the shoulder 160, prevent the wire 154 from falling out of the drive shaft 14.

The retaining mechanism 152 may be used on drivers having drive tips axially aligned with longitudinal axes of the drivers to hold a screw upon the drivers prior to screw insertion, and the retaining mechanism 152 is not limited to use with angled drivers. The retaining mechanism 152 may also be constructed in such a way that the fit of the wire 154 in the cannula 145 of screw 144 limits the depth that the drive shaft 14 may be inserted into the drive recess 143.

The proximal end 24 of the operating shaft 12 extends beyond the proximal end 44 of the sleeve 18. A cylindrical aperture 46 to receive a set screw is formed in the proximal extension and is disposed radially with respect to the longitudinal axis of the operating shaft 12.

The sleeve 18 has an outer diameter substantially the same as the outer diameter of barrel 28 at the distal end of the sleeve to form a smooth external profile with the barrel. The sleeve 18 has an inner diameter sized to closely receive the outer diameter of the operating shaft 12 while still permitting the operating shaft 12 to rotate relative to the sleeve 18.

Handle 22 is preferably made of stainless steel and includes a forward static handle section 84, securing sleeve 18, and a rearward movable handle section 86, rotatable relative to the forward section 84.

Forward handle section 84 is of hollow construction and has a cylindrical wall 88 defining an open proximal end and a tapered wall 90 distally joined to cylindrical wall 88 and terminating at a front wall 92. Wall 90 is tapered in a distal direction and is flared adjacent to front wall 92 to define an external profile that facilitates grasping during use. Concentric ribs 94 are provided along an external surface of the forward handle section 84 to facilitate gripping during use. A cylindrical bushing 96 is disposed in the open proximal end of the forward handle section 84. The bushing 96 has an annular, peripheral flange 98 at a forward face thereof abutting an internal annular shoulder 100 of the cylindrical wall 88. A central opening is formed in bushing 96 for securing the proximal end 44 of the sleeve 18 therein. Bushing 96 and sleeve 18 are preferably welded to the forward handle section 84 to form a sealed, water-tight cavity.

Rearward handle section 86 is of hollow construction, having a cylindrical wall 102 defining an open distal end that is closed by end cap 104. A cylindrical bushing 106 is disposed in the open distal end of the rearward handle section 86. The bushing 106 has an annular, peripheral flange 108 at a forward face thereof, and annular rim 110, extending axially in a direction distal from the flange 108, and a central, cylindrical protrusion 112 extending in a proximal direction. The bushing 106 is axially in disposed in the open face front end of the rearward handle section 86 with flange 108 abutting an internal shoulder 114 of cylindrical wall 102. An axial cavity is formed in bushing 106, extending proximally from the forward face thereof into the protrusion 112, for mounting the proximal end 24 of the operating shaft 12. Bushing 106 is preferably welded to the rearward handle section 86 to form a sealed, water-tight cavity. Longitudinal ridges 116 are provided along an external surface of the rearward handle section 86 to facilitate gripping during use. A pair of set screws 120 is used to couple the rearward handle section 86 to the operating shaft 12. The screws are disposed in a cylindrical passage formed in the bushing 106, radially disposed with respect to the longitudinal axis of the operating shaft 12 and in communication with the axial cavity of the bushing, the cylindrical passage being aligned with an opening in the cylindrical wall of 102 of the rearward handle section 86.

The forward handle section 84 is assembled with the rearward handle section 86, in such a way that the cylindrical wall of 88 within the distal end of the forward handle section 84 abuts the cylindrical wall 102 of the rearward handle section 86 at a junction 124. A ring 126, preferably made of stainless steel, is disposed concentrically around the handle 22 to extend over the junction 124, the ring 126 being mounted in grooves in the forward and rearward handle sections, while creating a stainless to stainless bearing surface that minimizes friction between the relatively movable components of the handle 22, to provide a good tactile response during use. A thrust washer 122 is disposed concentrically within rim 110 abutting the forward face of the bushing 106 such that the rearward handle section 86 can be assembled with the forward handle section 84 with the thrust washer 122 abutting a rearward face of bushing 96 and rim 110 extending along the cylindrical wall 88 within the distal end of the forward handle section 84.

Handle 22 is of lightweight, ergonomic construction to provide a balanced feel for a surgeon during use. During use, upon rotation of the rearward handle section 86 relative to the forward handle section 84, the operating shaft 12 will be rotated relative to sleeve 18, causing rotation of drive shaft 14 and the drive tip 52.

Figure 3:
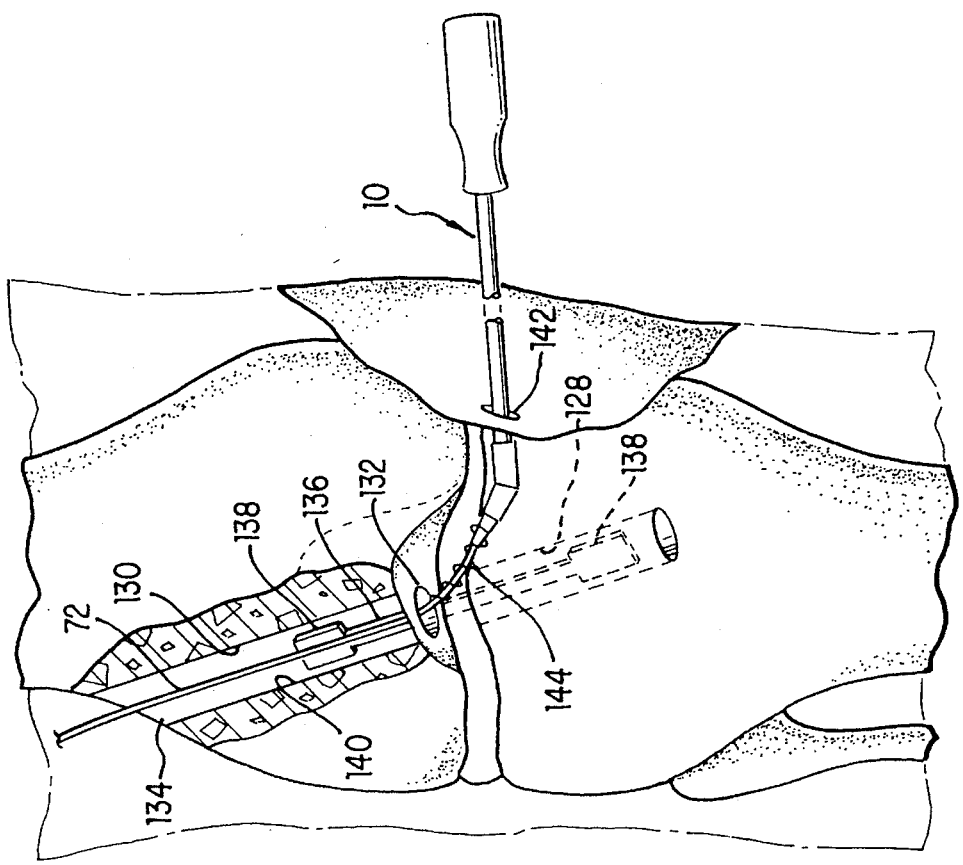
FIG. 3 is a front view, partly in section, of the joint of a right knee positioned at substantially 90°, showing the angled surgical screwdriver of FIG. 1 approaching an open end femoral bone tunnel via an anterolateral portal.
Figure 3A:
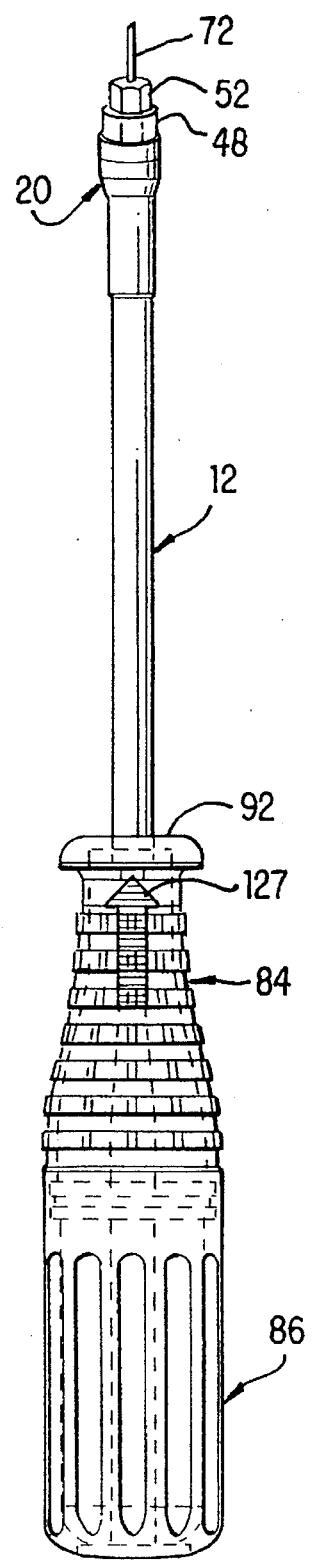
FIG. 3A is a top view of the angled surgical screwdriver of FIG. 1.

As shown in FIG. 3A, indicator 127, here an arrow is provided along an external surface of the forward handle section 84 to indicate, from a position external of the body, the orientation of the drive tip 52 when inserted in the body through an endoscopic portal. The indicator 127 is disposed on the same side of handle 22 as the drive tip 52 and is aligned with the drive tip 52 and the longitudinal axis of the surgical screwdriver 10 such that, with the indicator 127 facing a surgeon, the drive tip 52 will be oriented in a direction angularly upward relative to the longitudinal axis of the surgical screwdriver. The indicator 127 may utilize a wide range of suitable symbols, including arrows, lines or dots, and may be formed on the handle in diverse ways, such as by laser etching, engraving, or chemical deposition. Where formed as an indentation in the surface of the forward handle section 84, the indicator 127 can provide a tactile, as well as a visual, indication of the position of the drive tip 52.

The angled driver of the embodiment described herein includes numerous design features that facilitate its use in arthroscopic anterior cruciate ligament reconstruction. At the drive tip, the walls of the cylindrical section 74 and the nose section 76 have a minimal thickness to reduce the overall outer diameter of the angled surgical screwdriver 10 in the area of bend 78, and the distance that the angled surgical screwdriver 20 protrudes distally beyond bend 78 is minimized to enhance maneuverability of the driver within the close confines of the knee joint and to allow the use of smaller portals in arthroscopic cruciate ligament reconstruction. The minimal diametric dimension and distal taper of the nose section facilitate insertion of the driver in bone tunnels, allowing the drive shaft 14 to be inserted in bone tunnels up to bend 78. Shoulders 50 and 58 give the drive head 14 a distal taper, facilitating insertion in portals of minimal size and additionally enhance maneuverability at the knee joint. The drive shaft 14 protrudes beyond the back end of the bone screw 144 and spaces the bone screw distally from the bend 78 a greater amount, such that the bone screw can be inserted that much further into a bone tunnel with the driver inserted in the bone tunnel up to the bend 78. According to a preferred embodiment, the outer diameter of the angled driver 10 at bend 78 is approximately 0.350 inches (8.9 mm), and the distance that the driver protrudes distally of bend 78 is approximately 0.710 inches (18.0 mm).

Figure 9:
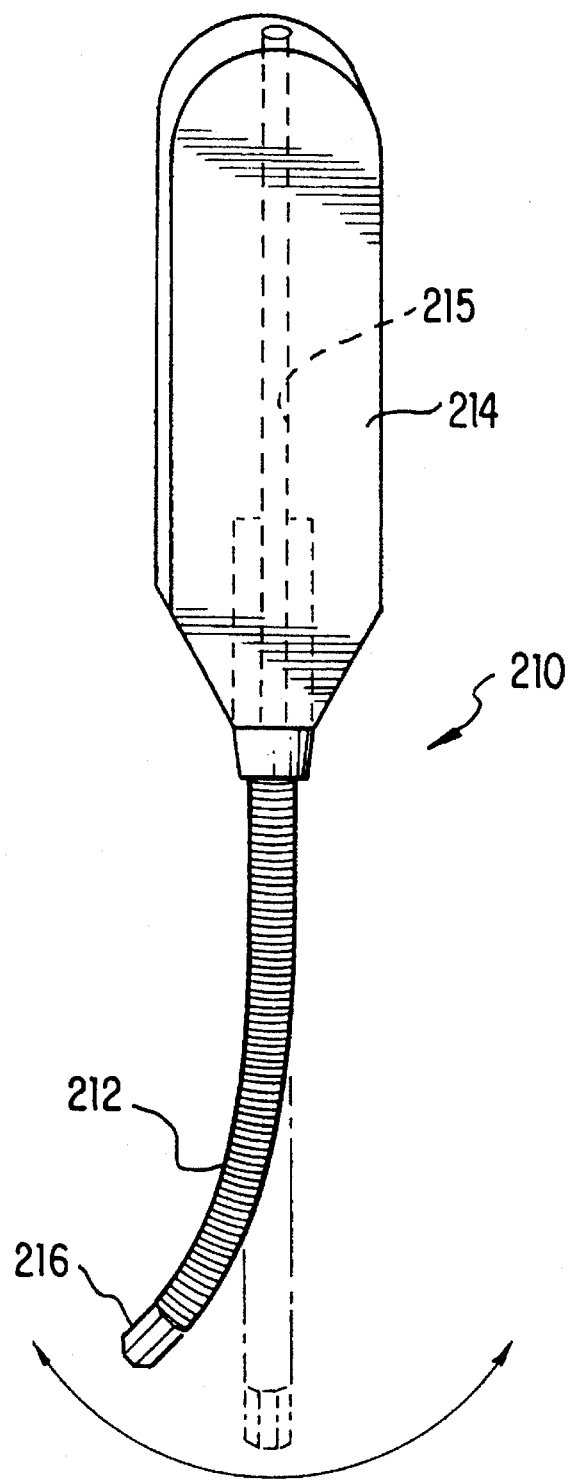
FIG. 9 is an isometric view of a cannulated flexible screwdriver of the present invention.
Figure 10:
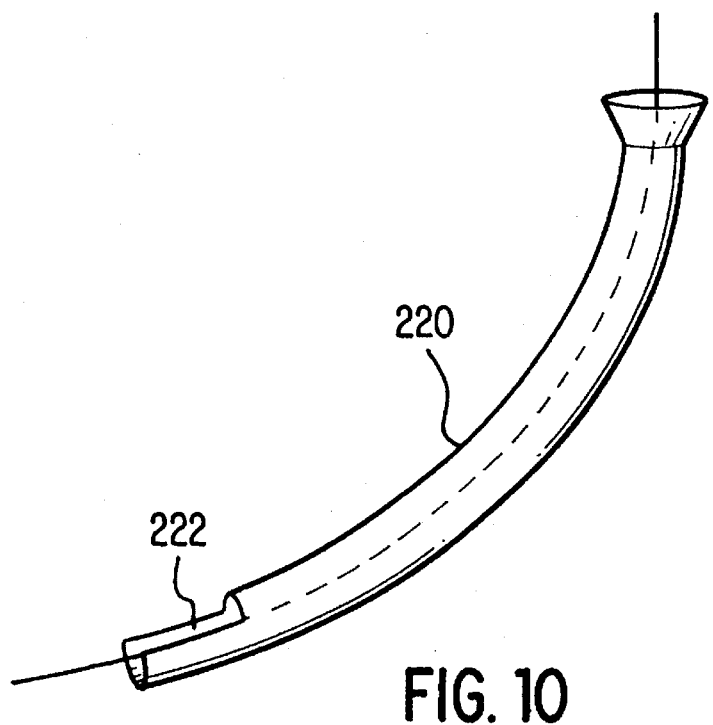
FIG. 10 is an isometric view of a curved cannula for use with the screwdriver of FIG. 9.

In accordance with the present invention, an angled surgical screwdriver can be achieved by providing a flexible drive shaft. In addition, the capability of guiding the angled screwdriver along a guide wire may be made possible by providing a cannulation through the drive shaft and the handle of the screwdriver. Referring now to FIG. 9, a flexible cannulated screwdriver 210 is shown. A flexible drive shaft 212 may be formed by two or more concentric wire coils. The coils are wound in opposite directions, one being clockwise and another counterclockwise. The coils advantageously leave a tunnel through the center of the shaft through which a guide wire may be inserted. A handle 214 is attached to one end of the drive shaft. The handle 214 has a longitudinal tunnel or cannula 215 in alignment with the tunnel through the flexible shaft 212. At the distal end of the drive shaft 212, a drive tip 216 is mounted. The drive tip 216 is configured to engage a drive recess or drive protrusion at the rear of a screw. The drive tip 216 is cannulated to receive a guide wire that will pass through the shaft and handle of the driver. The spiral coils are advantageously flexible so that the drive shaft can assume a wide range of angles for driving a screw into its desired location. By providing two oppositely wound coils, the screwdriver can be used to transmit rotational movement in either a clockwise or counterclockwise direction. In one rotational direction, one of the coils tightens and rotates the drive head. In the opposite rotational direction, the other spiral coil tightens and rotates the drive head in the opposite rotational direction. If the screwdriver is to be used only for rotation in a single direction, it would be sufficient to use a single spiral coil. Moreover, other materials beside spiral coils may provide the requirements of flexibility and rotational stiffness. For example, the shaft may possibly be formed by a Nitinol tube. Therefore, the use of such other materials and constructions as are well known to those of ordinary skill in the art are included for use within the scope of the present invention of a flexible cannulated surgical screwdriver.

A curved sheath 220 may be used in conjunction with the guide wire to assist in protecting surrounding tissue from the screw threads. In accordance with a presently preferred embodiment of the curved sheath 220, an opening or slot 222 is provided at the distal end of the sheath to permit direct visualization of the screwdriver tip as it enters the bone tunnel.

Figure 11:
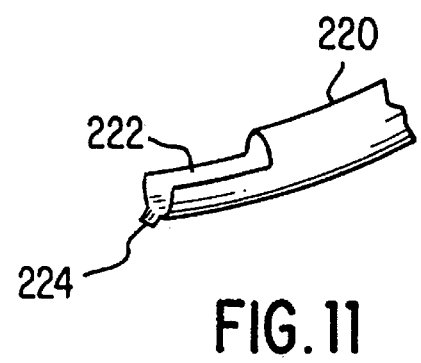
FIG. 11 is a broken view of an alternate embodiment of the curved cannula of FIG. 10.

The curved sheath may be modified as shown in FIG. 11 to add a sharp flange 224 projecting from the distal end of the curved sheath away from the sheath. The sharp flange 224 may be dug into a bone portion of the graft so as to hold the graft in place during interference screw fixation.

In accordance with a presently preferred embodiment of the cannulated flexible screwdriver of the invention, reference now is made to FIGS. 12 and 13. The handle 214 is designed to give the surgeon enough leverage to apply sufficient torque upon an interference screw. However, care is taken in designing the handle to help avoid application of too much torque. For example, the handle on a driver for bio-absorbable screws is made narrower because such screws cannot withstand as much torque as a stainless steel screw. The presently preferred handle dimensions for driving steel screws are ¾ inches (2 cm) thick and 1½ inches (3.8 cm) wide at its widest portion. The choice of dimensions depend upon the type of screw to be used with the driver.

An optional locking screw 230 may be provided on the handle for clamping onto the guide wire when it is within the cannula of the driver. This can be helpful in removing the guide wire from the bone tunnel after the interference screw has been properly secured between a bone graft and the bone tunnel wall. After the screwdriving procedure is completed, the locking screw 230 may be tightened against the guide wire. Then by pulling on the handle of the screwdriver the guide wire is removed from the bone tunnel. The locking screw 230 may be made in several parts for ease of manufacture. A threaded screw 232 is held within a bushing 234. A knob 236 attaches to the bushing to facilitate manual rotation of the screw.

The screwdriver shaft may also be formed out of several parts. Secured to the handle in the embodiment of FIG. 12 is a stiff cannulated shaft 242. The stiff shaft 242 may be made from stainless steel. A counterbore is provided at the distal end of the stiff shaft for accepting the flexible members 244.

The flexible member 244 of the present embodiment is formed by four concentric coil springs. The concentric coil springs fit closely over one another. This prevents a windup delay in the transmission of torque when the handle is rotated. The concentric coil springs alternate from innermost to outermost between clockwise and counterclockwise helixes. While the clockwise springs tighten and transmit torque, the counterclockwise springs open up. When the driver is rotated in the opposite direction, the counterclockwise springs tighten while the clockwise springs open. If the pitch of the coils is small as in the case for a single wire, the coils might interengage during application of torque. To prevent this, each spring is made with from about three to ten wires. The wires are wound in parallel to form a helix of a single diameter. The reason a plurality of wires is used in each spring is to give the wires of the spring a steeper pitch. With the steeper pitch, during application of torque, adjacent concentric springs will hit against each other with wire strands roughly at right angles to one another. When the inner spring expands, the outer spring contracts. The pitched wires prevent interengagement while permitting torque transmission.

The proximal end of the flexible member 244 is soldered or attached by some other conventional method within the counterbore of the stiff shaft 242. The distal end of the flexible member 244 is soldered or otherwise attached to a drive tip 246. The drive tip 246 has a head, as described above for the angled driver, shaped for engagement with the proximal end of a screw. The drive tip 246 of the flexible driver is cannulated for fitting over a guide wire.

About the outside of the flexible member 244 is a heat shrinked plastic tube. The plastic tube is preferably made from an autoclavable material.

The surgical screwdrivers described herein are useful for arthroscopic ligament reconstruction procedures of the knee and of other joints in the human body. The knee is an example of a moveable joint that sustains injury to connective tissue with relative frequency. Although the surgical screwdrivers are described herein as applicable to methods of anterior cruciate ligament reconstruction, the surgical screwdriver according to the present invention can also be used in reconstructing posterior ligaments of the knee. Other joints also rely on ligaments to maintain function. In all joints, ligaments play an important role in holding the different bones of the joints in alignment.

A method of least invasive, or arthroscopic, anterior cruciate ligament reconstruction according to the present invention is shown in FIG. 3. An incision of minimal size is made medial to the tibial tubercle and distal to the joint line to harvest a portion of the patellar tendon which will serve as a graft ligament. Subsequently, this incision can be utilized as the portal 142 for inserting surgical instruments to fix one end of the graft ligament in the femoral bone tunnel as described below, and may also be used for access to the region of the cruciate ligament attachment sites to help determine proper placement of the tibial and femoral bone tunnels, with the knee being visualized with an arthroscope.

Tibial bone tunnel 128 and femoral bone tunnel 130 are formed respectively in the tibia and femur. The femoral bone tunnel is formed by instruments inserted in a cephalad direction through the tibial bone tunnel. The femoral bone tunnel 130 is formed as an open-ended longitudinally straight, cylindrical tunnel extending from an opening 132 on the femoral condyle at the attachment site of the anterior cruciate ligament on the femur to an opening 134 on the lateral femoral cortex with (in one embodiment of the method) soft tissue covering the lateral femoral cortex remaining intact. The central longitudinal axis of the femoral bone tunnel is therefore substantially offset from the portal 142.

A ligament 136, such as a prosthetic ligament or the graft ligament harvested as previously described, having bone blocks 138 or other suitable terminus at its ends, is inserted initially through the tibial bone tunnel 128 and into the femoral bone tunnel 130 via a puncture wound. (The puncture wound is in line with opening 134 on the lateral femoral cortex and forward proximally and laterally on the patient's thigh.) A rigid pushing rod may be used to help push the graft through the tibial tunnel and into the femoral tunnel. The ligament 136 is then positioned so as to extend across the knee joint with a bone block 138 or other terminus positioned in each of the bone tunnels 128 and 130. A guide wire is inserted through the portal 142 into the femoral tunnel alongside the ligament 136. The guide wire is used to guide a bone screw positioned on a driver to the bone block at the end of the graft ligament for the purposes of securing the ligament with the screw. The guide wire 72 is made from a material such as a nitinol wire and is typically on the order of 14 inches (36 cm) in length. It is inserted into the tibial bone tunnel 128 and through the femoral tunnel 130, with the guide wire 72 exiting the knee through the soft tissue adjacent the lateral femoral cortex. Alternatively, the guide wire 72 can be inserted through the opening 134 on the lateral femoral cortex via the puncture wound described previously.

The guide wire 72 is disposed parallel with the bone block 138 and the wall 140 and, therefore, parallel with the central longitudinal axis of the femoral bone tunnel. If the guide wire is inserted first through the puncture wound, it is advanced until an end of the guide wire 72 is visible at the knee joint. The visible end of the guide wire is grasped and disposed externally of the knee, creating a substantial bend in the guide wire 72, as shown in FIG. 3, using an instrument which is inserted through an anteromedial or anterolateral portal. The bend in the guide wire is due to the fact that the portal 142 is substantially offset from, and not aligned with, the central longitudinal axis of the femoral bone tunnel 130. A bone screw 144 having a cannula 145, in the form of a central, coaxial, longitudinal passage therein, is mounted on the end of the guide wire 72 externally of the knee, the cannula having a diameter slightly larger than the diameter of the guide wire 72. The end of the guide wire 72 is frictionally secured in the cylindrical passage 62 of the drive tip 52. The bone screw 144 is moved along the guide wire and mounted on the drive tip 52 by drive recess 143. Since the drive recess is coaxial with the cannula, the drive shaft 14 protrudes from the back end of the bone screw 144 by about 5 mm.

With the knee at an angle of substantially 90°, the angled screwdriver 10 is inserted at the knee joint via the portal 142. The driver is guided into the femoral bone tunnel 130 through the opening 132 on the femoral condyle by simultaneously turning and pushing the driver with the drive tip 52 oriented upwardly. The orientation of the drive tip is indicated by the indicator 127 on the forward handle section facing the surgeon, as shown in FIG. 3A. The direction of insertion from the portal 142 to the femoral bone tunnel 130 is at a non-zero acute angle with respect to the central longitudinal axis of the femoral bone tunnel because the portal 142 is not aligned with the femoral bone tunnel axis. The angled screwdriver 10, as guided by the guide wire 172, is moved forward along the femoral bone tunnel 130, with the longitudinal axis of the drive shaft 14 disposed parallel with the longitudinal axis of the femoral bone tunnel; and, concurrently, the guide wire 72 is pushed cephalad in the tunnel and through the puncture wound.

Once the tip of the bone screw 144 is disposed adjacent the bone block 138, the rearward handle section 86 of the angled screwdriver is manually rotated relative to the forward handle section 84, while the forward handle section is grasped and held fixed, to rotate the operating shaft 12 relative to the sleeve 18. Consequently, the drive shaft 14 (the driven end), driven by handle 22, drives the screw 144 in a direction that is at a non-zero acute angle with respect to the handle (i.e, the driving end) of the angled screwdriver. Accordingly, the bone screw 144 is driven in a forward direction in the femoral bone tunnel 130 laterally between the bone block 138 and the wall 140 and parallel to the bone block 138 and the wall 140. A thread on the screw engages the tunnel wall 140 and the bone block 138 along the length of the bone block to fixate the ligament 136. The bone screw is driven externally of the knee from a direction offset from the direction of bone screw insertion and with the knee at an angle of substantially 90° such that the hyperflexion is avoided. The bone screw 144 is driven an additional 5 mm into the femoral bone tunnel 130 due to the exposed portion of the drive shaft 14 at the back end of the screw, allowing a countersink below the opening 132.

The angled screwdriver 10 is then pulled away from the screw 144 for removal through portal 142, and the guide wire 72 can be removed with the driver 10 or pulled away from the driver 10 for removal via the puncture wound in the soft tissue adjacent the lateral femoral cortex. The bone block 138 in the tibial bone tunnel 128 is then fixated by inserting a bone screw in the tibial bone tunnel and driving the bone screw parallel to the bone block and a wall of the tibial bone tunnel.

It will be appreciated that portal 142 can be the same portal utilized for alignment determination in forming the tibial and femoral bone tunnels, and that a single portal can be used throughout the procedure to harvest the patellar tendon graft, to orient the tibial and femoral bone tunnels, to help orient the graft ligament, and to insert the bone screw in the femoral bone tunnel.

It will also be appreciated that the drive shaft 14 of the surgical screwdriver can be offset from the handle 22 by the bend 78 or a curve as well as other configurations and that the bend, curve or other configuration can be rigid or flexible. The angled surgical screwdriver 10 can be used with or without the guide wire 72.

A related embodiment of the method of arthroscopic, anterior cruciate ligament reconstruction is shown in FIG. 5. Instead of the femoral bone tunnel being formed as an open-ended tunnel, the femoral bone tunnel 130 is formed as a blind, or closed-ended tunnel extending from an opening 132 on the femoral condyle to an end wall 172 such that the femoral bone tunnel does not broach the lateral femoral cortex.

A graft or prosthetic ligament 136 having bone blocks 138 at its ends is inserted in the tibial bone tunnel 128 via the portal to extend across the knee joint with a bone block 138 disposed in each of the bone tunnels of the femur and the tibia.

A bone screw 144 is mounted on the angled screwdriver 150 externally of the knee. The drive tip 52 of the driver is engaged in the drive recess of the screw and the retaining mechanism 152 is received in the cannula of the screw. In this configuration, the drive shaft 14 protrudes beyond the back end of the screw 144 substantially 5 mm. The curve of the distal cylindrical section 158 of the wire 154 provides frictional engagement in the cannula of the screw 144. The screw is positively held by the retaining mechanism 152 upon the angled driver 150 prior to screw insertion. This arrangement allows manipulation of the screw at the knee joint while avoiding disengagement of the screw from the driver and possible loss of the screw in the knee.

With the knee at an angle of substantially 90°, the angled driver 150 with the screw 144 held thereon by retaining mechanism 152 is inserted at the knee joint via an anteromedial or anterolateral portal, such as anteromedial portal 174. The driver and screw are guided into the femoral bone tunnel 130 through the opening 132 on the femoral condyle. The drive tip 52 remains pointed upwards as indicated by indicator 127 facing the surgeon. The direction of insertion from the portal 174 to the femoral bone tunnel 130 is at a non-zero acute angle with respect to the central longitudinal axis of the femoral bone tunnel. The angled driver 150 is advanced along the femoral bone tunnel 130 in a direction parallel with the bone block 138 and the wall 140, and therefore, parallel with the longitudinal axis of the femoral bone tunnel until the bone screw 144 is positioned laterally between the bone block 138 and a wall 140 of the femoral bone tunnel as shown in FIG. 5.

Once the tip of the bone screw 144 is disposed adjacent the bone block 138, the rearward handle section 86 of the angled driver 150 is rotated relative to the forward handle section 84 while the forward handle section 86 is held fixed, to drive the bone screw 144 into the femoral bone tunnel 130 as described in connection with FIG. 3, and to fixate the ligament 136. Again the longitudinal axis of the operating shaft 12 is angularly disposed with respect to the direction of insertion. The screw is inserted an additional 5 mm into the femoral bone tunnel 128 and driven parallel with the bone block 138 in the tibial bone tunnel.

As in the case of FIG. 3, portal 174 can be the same portal as utilized in orienting the tibial and femoral bone tunnels, and a single portal can be used to harvest the patellar tendon graft, to orient the tibial and femoral bone tunnels, and to fixate the ligament in the femoral bone tunnel.

A guide wire can be used with the angled driver 150 by being driven into the femur to guide the driver during screw insertion. Such a guide wire can be used with the retaining mechanism 152, or in place of the retaining mechanism 152, or as a retaining mechanism by lengthening the distal cylindrical section 158.

Figure 14:
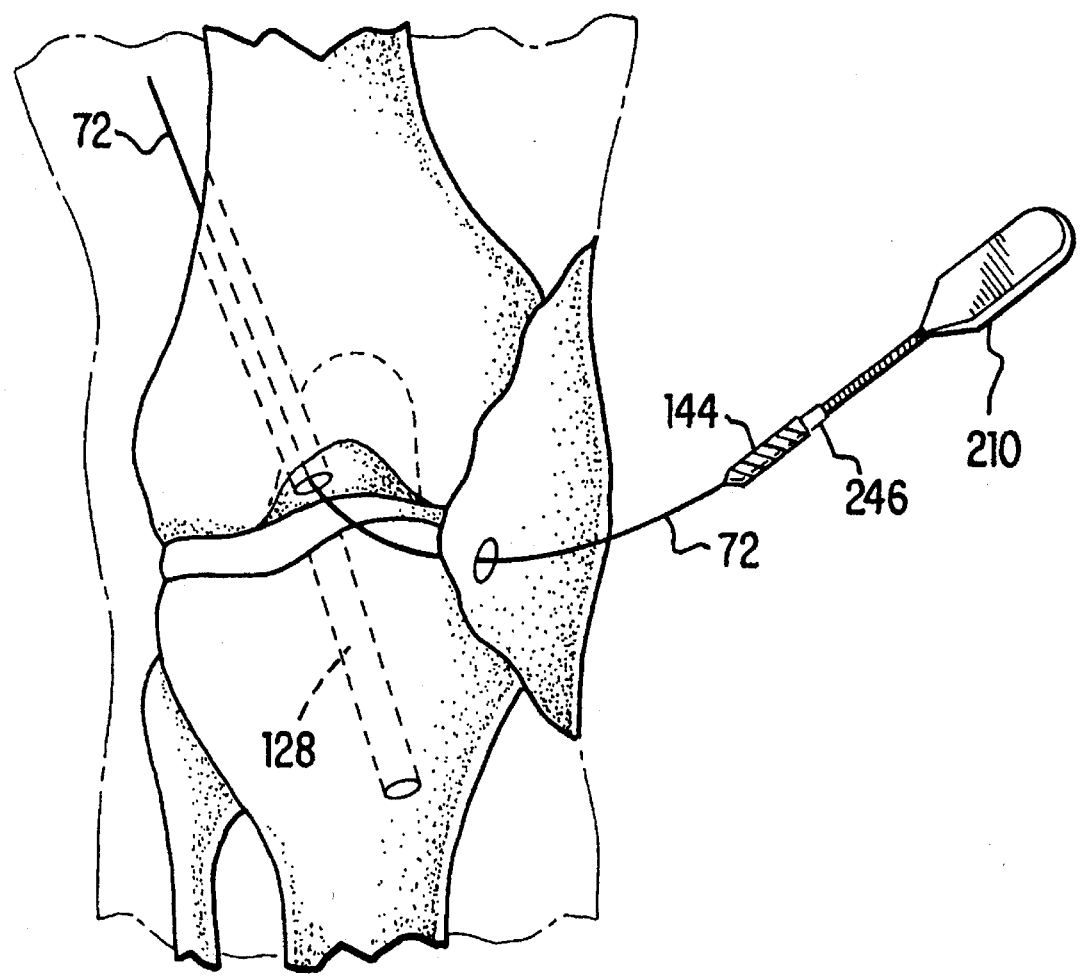
FIG. 14 is a front view, partly in section, of the joint of a knee, showing the screwdriver of FIG. 9 approaching a femoral tunnel via a curved cannula inserted through an anterolateral portal.

As an alternative to the angled driver described above, the invention also provides, in a further embodiment, a method of arthroscopic, anterior cruciate ligament reconstruction using the flexible cannulated screwdriver 210 as shown in FIG. 14. The femoral tunnel may be formed as an open-ended tunnel or as a blind, or closed ended tunnel. The femoral tunnel may be drilled through the tibial tunnel with the knee at approximately 50 degrees of flexion. The flexible cannulated screwdriver used along a guide wire may be substituted for the angled driver in above-described methods or the following method may be employed advantageously. A graft or prosthetic ligament 136 having bone blocks 138 at its end is inserted in the tibial bone tunnel 128. A pushing rod may be used to push the graft across the knee joint into the femoral tunnel so that one bone block 138 is disposed in each of the bone tunnels of the femur and the tibia. The knee is placed at 90 degrees of flexion for insertion of the screw. With the knee in this position, the ligament advantageously drops back away from the path of the interference screw. A guide wire 72 is inserted through the anteromedial portal 142 into the femoral tunnel alongside the bone block 138 therein. If desired, the curved sheath 220 may be slid over the guide wire to protect surrounding tissue from the screw threads before the screw is driven into engagement with the bone block and bone tunnel. However, with the knee placed at about 90° the sheath is generally not required. A cannulated interference screw 144 is mounted onto the guide wire 72. The flexible cannulated screwdriver is then mounted on the guide wire such that the drive tip 246 of the screwdriver engages the screw. The driver and screw are guided into the knee joint along the guide wire through the anteromedial portal. The driver and screw continue along the wire through the femoral condyle into the femoral bone tunnel. The shaft of the driver advantageously bends along the guide wire from the anteromedial portal into the bone tunnel. The screw is driven between the bone block and the wall parallel with the longitudinal axis of the femoral bone tunnel. Rotation of the driver handle is transmitted by the shaft to the screw. Once the screw is satisfactorily secured, the driver is pulled out back along the guide wire. If desired, the locking screw on the driver handle can be tightened upon the guide wire so that the guide wire is removed along with the driver.

A related embodiment of an angled driver according to the present invention is shown at the distal end in FIGS. 6 and 7 as item 180, which is similar to the angled driver 150, and includes a drive head housing 20 mounting the drive shaft and a distal end of the operating shaft, the drive shaft including a drive tip 52 having a hexagonal configuration in cross-section for engaging a hexagonal drive recess 143 of an interference bone fixation screw 144.

Drive head housing 20 of angled driver 180 is formed integrally with sleeve 18 and includes a flared section 182 distally joined to the sleeve 18, an intermediate cylindrical section 184 joined to flared section 182 and an angled section 186 joined to intermediate section 184. The flared and intermediate sections 182 and 184 are axially aligned, while the angled section 186 is angularly offset from the flared and intermediate sections such that a longitudinal axis of the angled section is disposed at an angle, with respect to a longitudinal axis of the flared and intermediate sections, that is substantially the same as the angle that the longitudinal axis of the drive shaft is disposed with the longitudinal axis of the operating shaft.

The drive tip 52 of the angled driver 180 is formed of six facets for engaging the drive recess 143 of the bone screw 144. Drive tip 52 can have a configuration in cross-section that is substantially constant along the length of the drive tip as shown in FIG. 6, or the drive tip 52 can be tapered or stepped in a distal direction to further facilitate insertion through very small portals and mobility at the knee joint. It includes a cylindrical passage 62 coaxial with the drive shaft as shown in FIG. 7, for securing retaining mechanism 152. Retaining mechanism 152 includes a wire 154 press fit into passage 62 and having a distal cylindrical section 158 protruding beyond the drive tip 52. The distal cylindrical section 158 is formed with a thermally set, angled bend along a longitudinal axis of the wire 154, the bend being offset from the longitudinal axis of the drive shaft for being disposed in the cannula 145 of the bone screw 144. The bone screw is mounted on drive tip 52 such that the screw will be forced slightly out of axial alignment with the drive tip 52 to produce frictional engagement of the drive tip in the drive recess of the screw to resist disengagement of the screw from the angled driver prior to screw insertion as shown in FIG. 6.

A further modification of an angled driver according to the present invention is shown in FIG. 8 at 190, in which the bone screw is mounted on drive tip 52 without forcing the screw out of axial alignment with the drive tip. In all other respects, angled driver 190 is substantially the same as angled driver 180.

Both angled drivers 180 and 190 and the flexible cannulated screwdriver can be utilized for insertion of bone screws, in arthroscopic cruciate ligament reconstruction in bone tunnels from directions offset from the direction of screw insertion and from portals not aligned with the bone tunnels as previously described; and, the angled screwdriver 180 can be used with or without a guide wire.

The screwdrivers described herein allow bone screws to be inserted in bone tunnels parallel with walls of the bone tunnels and bone blocks in the bone tunnels to obtain maximum thread purchase along the entire length of the bone blocks with the screws being driven from directions offset from the direction of screw insertion. Bone screws can be inserted in femoral bone tunnels directly from anteromedial or anterolateral portals and without accessing the femoral bone tunnels through the tibial bone tunnels. For example, bone screws can be inserted in the femoral bone tunnels with the knee positioned at an angle of substantially 90°. The present invention removes the undesirable requirement for hyperflexion of the knee in order to insert bone screws.

In addition, the same portal can be employed to perform procedures preparatory to graft fixation, to orient the tibial and femoral bone tunnels and to insert interference screws in the femoral bone tunnel, thereby eliminating the need for portals in soft tissue adjacent the lateral femoral cortex specifically formed for the purpose of inserting bone screws in the femoral bone tunnel. Using the methods of this invention, trauma and invasiveness are minimized.

The surgical screwdriver and its methods of use described above for anterior cruciate ligament reconstruction of the knee can also be applied to other ligament reconstruction procedures including arthroscopic posterior cruciate ligament reconstruction of the knee. In the latter case, the driver provides a means to insert bone screws in bone tunnels in a direction parallel with walls of the bone tunnels and bone blocks in the bone tunnels to fixate a graft or prosthetic ligament in the anatomic position of the posterior cruciate ligament while introducing the screws through portals not aligned with the direction of screw insertion. The flexible cannulated screwdriver advantageously accommodates a wide range of angles between the portal and the tunnel.

Further details concerning practice of the present invention are described by David A. McGuire, M.D., an inventor herein, in the brochure entitled "The Paramax ACL Guide System Surgical Technique", and incorporated herein by reference (published by Linvatec Corporation, Largo, Fla. 34643) submitted herewith.

Inasmuch as the present invention is subject to many variations, modifications and changes in detail, it is intended that the subject matter discussed above and shown in the accompanying drawings may be interpreted as illustrative not in a limiting sense.

I claim:

1. A screwdriver comprising:

a handle having a longitudinal cannula;

a flexible hollow shaft having a proximal end coupled to said handle and a distal end; and a cannulated drive tip coupled to the distal end of said flexible shaft for being rotated upon rotation of said shaft, wherein a guide wire may be inserted into the cannulated drive tip through said flexible hollow shaft and out through said handle.

2. The screwdriver of claim 1 wherein said flexible hollow shaft comprises a plurality of concentric coils.

3. The screwdriver of claim 2 wherein said plurality of concentric coils includes at least one clockwise wound helical coil and at least one counterclockwise wound helical coil.

4. A surgical screwdriver for driving screws in bone comprising:

a flexible shaft having a distal end and a proximal end and being hollow along a longitudinal axis;

a handle coupled to the proximal end of said flexible shaft and having a longitudinal tunnel; and a cannulated tip on the distal end of said flexible shaft for engaging a cannulated screw on a guide wire.

5. The surgical screwdriver of claim 4 wherein the cannulated tip is elongated so that when the tip engages the cannulated screw, a portion of the tip protrudes beyond the proximal end of the screw by a distance, so as to allow the screw to be driven into the bone until its proximal end lies beneath the bone surface by such distance.

6. The surgical screwdriver of claim 5 wherein such distance is approximately 5 mm.

7. The surgical screwdriver of claim 4 wherein said flexible shaft comprises a plurality of concentric coils.

8. The surgical screw driver of claim 7 wherein adjacent ones of said concentric coils are spiralled in opposite directions.

9. A method of interference screw fixation comprising:

forming a bone tunnel having a tunnel wall and a central longitudinal axis in a bone;

positioning a bone block within the bone tunnel;

introducing a guide wire into said bone tunnel alongside the bone block and through a portal that is substantially offset from the central longitudinal axis;

mounting a cannulated interference screw on the guide wire;

mounting a cannulated screwdriver, having a handle coupled to a flexible shaft, onto the guide wire so as to engage the cannulated interference screw;

moving the screwdriver and screw along the guide wire as it curves from the portal into the bone tunnel until the screw contacts the bone block and the bone tunnel wall; and rotating the screwdriver to drive the screw and fix the bone block within the bone tunnel.

10. The method of claim 9 wherein the step of rotating includes driving the screw in the bone tunnel in a direction of insertion parallel with the central longitudinal axis of the bone tunnel with the axis of the handle of the screwdriver disposed at a non-zero angle with respect to the central longitudinal axis of the bone tunnel.

11. The method of claim 9 further comprising mounting a curved sheath onto the guide wire and wherein the screwdriver and the screw are moved in through the sheath along the guide wire.

* * * * *